US009179827B2

(12) United States Patent
Hastings et al.

(10) Patent No.: US 9,179,827 B2
(45) Date of Patent: Nov. 10, 2015

(54) SYSTEMS AND METHODS FOR DETERMINING THE POSITION AND ORIENTATION OF MEDICAL DEVICES INSERTED INTO A PATIENT

(75) Inventors: Roger N. Hastings, Maple Grove, MN (US); Michael J. Pikus, Golden Valley, MN (US); Kevin D. Edmunds, Ham Lake, MN (US); Leonard B. Richardson, Brooklyn Park, MN (US); Frank Ingle, Palo Alto, CA (US); Josef Koblish, Sunnyvale, CA (US); Tat-Jin Teo, Sunnyvale, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 673 days.

(21) Appl. No.: 12/958,610

(22) Filed: Dec. 2, 2010

(65) Prior Publication Data
US 2011/0144479 A1 Jun. 16, 2011

Related U.S. Application Data

(60) Provisional application No. 61/286,674, filed on Dec. 15, 2009.

(51) Int. Cl.
*A61B 5/00* (2006.01)
*A61B 1/04* (2006.01)
*A61B 5/06* (2006.01)
*A61B 5/07* (2006.01)
*A61B 19/00* (2006.01)

(52) U.S. Cl.
CPC .................. *A61B 1/041* (2013.01); *A61B 5/061* (2013.01); *A61B 5/07* (2013.01); *A61B 5/6861* (2013.01); *A61B 2019/2253* (2013.01)

(58) Field of Classification Search
CPC ........... A61B 1/041; A61B 2019/2253; A61B 5/061; A61B 5/07; A61B 5/6861; A61B 19/5244; A61B 2019/5251
See application file for complete search history.

(56) References Cited

U.S. PATENT DOCUMENTS

| 6,945,938 | B2 | 9/2005 | Grunwald |
| 7,306,561 | B2 | 12/2007 | Sathyanarayana |
| 2003/0181788 | A1* | 9/2003 | Yokoi et al. .................. 600/160 |
| 2006/0061354 | A1* | 3/2006 | Wallance et al. ........ 324/207.15 |
| 2006/0100522 | A1 | 5/2006 | Yuan et al. |
| 2006/0173350 | A1 | 8/2006 | Yuan et al. |
| 2006/0253028 | A1 | 11/2006 | Lam et al. |
| 2007/0016054 | A1 | 1/2007 | Cao et al. |
| 2007/0038111 | A1 | 2/2007 | Rehrig et al. |
| 2007/0219405 | A1* | 9/2007 | Uchiyama et al. .............. 600/12 |

(Continued)

FOREIGN PATENT DOCUMENTS

JP WO 2007/040269 * 4/2007 ............... A61B 5/07

*Primary Examiner* — Amanda Lauritzen Moher
(74) *Attorney, Agent, or Firm* — Faegre Baker Daniels LLP

(57) ABSTRACT

A medical device system includes an elongated body with a distal end that is configured and arranged for insertion into a patient. A housing is disposed in the distal end of the body. A rotatable magnet is disposed in the housing. At least one magnetic field winding is configured and arranged to generate a magnetic field at the location of the magnet. The magnetic field causes rotation of the magnet at a target frequency. An array of magnetic field sensors is disposed external to the patient. The magnetic field sensors are configured and arranged to sense the location and orientation of the magnet in relation to the array of magnetic field sensors.

5 Claims, 9 Drawing Sheets

(56) References Cited

U.S. PATENT DOCUMENTS

| | | | |
|---|---|---|---|
| 2008/0167523 A1* | 7/2008 | Uchiyama et al. | 600/114 |
| 2009/0227840 A1* | 9/2009 | Uchiyama et al. | 600/118 |
| 2009/0281387 A1* | 11/2009 | Takizawa et al. | 600/117 |
| 2010/0179381 A1* | 7/2010 | Kawano et al. | 600/104 |
| 2010/0249603 A1 | 9/2010 | Hastings et al. | |
| 2010/0305426 A1* | 12/2010 | Kimura et al. | 600/411 |

\* cited by examiner

_US 9,179,827 B2_

SYSTEMS AND METHODS FOR DETERMINING THE POSITION AND ORIENTATION OF MEDICAL DEVICES INSERTED INTO A PATIENT

CROSS-REFERENCE TO RELATED APPLICATIONS

This application claims the benefit under 35 U.S.C. §119(e) of U.S. Provisional Patent Application Ser. No. 61/286,674 filed on Dec. 15, 2009, which is incorporated herein by reference.

TECHNICAL FIELD

The present invention is directed to the area of medical devices that are insertable into a patient and methods of making and using the medical devices. The present invention is also directed to position and orientation systems for determining the position and orientation of the medical devices within patients, as well as methods of making and using the medical devices and position and orientation systems.

BACKGROUND

Medical devices that are insertable into patients, such as imaging pills and catheters have proven diagnostic and therapeutic capabilities. Some medical devices are designed to perform one or more functions at one or more locations within a patient's body. Position and orientation systems may be used to determine the location of the medical device within the patient.

BRIEF SUMMARY

In one embodiment, a medical device system includes an elongated body with a distal end that is configured and arranged for insertion into a patient. A housing is disposed in the distal end of the body. A rotatable magnet is disposed in the housing. At least one magnetic field winding is configured and arranged to generate a magnetic field at the location of the magnet. The magnetic field causes rotation of the magnet at a target frequency. An array of magnetic field sensors is disposed external to the patient. The magnetic field sensors are configured and arranged to sense the location and orientation of the magnet in relation to the array of magnetic field sensors.

In another embodiment, a method for determining the position and orientation of a medical device inserted into a patient includes inserting the medical device into the patient. The medical device includes a rotatable magnet disposed in a housing. A magnetic field is generated at the location of the magnet to cause the magnet to rotate at a target frequency. The position and orientation of the housing is determined using a position and orientation system positioned external to the patient. The position and orientation system includes a plurality of magnetic field sensors that determine the position and orientation of the housing with respect to the magnetic field sensors.

In yet another embodiment, a medical device system includes an imaging pill configured and arranged for ingestion by a patient. A housing is disposed within the pill. A rotatable magnet is disposed in the housing. At least one magnetic field winding is configured and arranged to generate a magnetic field at the location of the magnet. The magnetic field causes rotation of the magnet at a target frequency. An array of magnetic field sensors is disposed external to the patient. The magnetic field sensors are configured and arranged to sense the location and orientation of the magnet in relation to the array of magnetic field sensors. The medical device system also includes electronics for capturing at least one image.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

Figure 1:
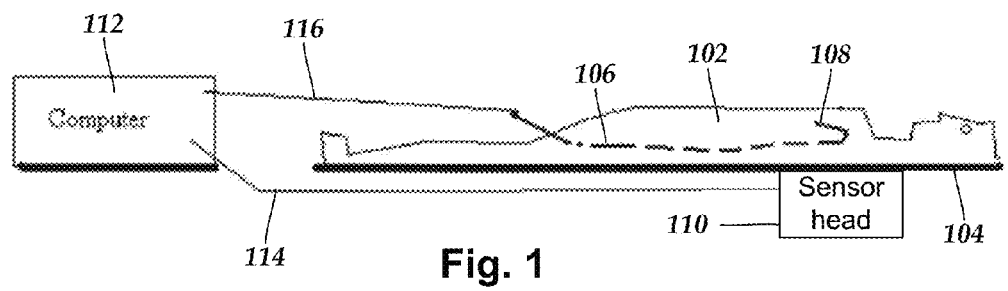
FIG. 1 is a schematic perspective view of one embodiment of a position and orientation system in communication with a medical device that is inserted into a patient, according to the invention.

The present invention is directed to the area of medical devices that are insertable into a patient and methods of making and using the medical devices. The present invention is also directed to position and orientation systems for determining the position and orientation of the medical devices within patients, as well as methods of making and using the medical devices and position and orientation systems.

Suitable medical devices include, but are not limited to, medical devices that are insertable into a patient and that include at least one magnet driven to rotate by a generated magnetic field and a position and orientation system in communication with the at least one magnet. In some embodiments, when the medical device is inserted into the patient, at least a portion of the medical device extends externally from the patient. In other embodiments, when the medical device is inserted into the patient, the medical device is completely contained inside the patient.

In at least some embodiments, the position and orientation system includes an array of magnetic field sensors. The array may include like magnetic field sensors chosen for a particular application. Suitable magnetic sensors include, for example, magnetic induction (wire wound around a magnetic core), flux gate magnetometers, saturable core magnetometers, Hall effect, Superconducting Quantum Interference Device ("SQUID") magnetometers, giant magnetoresistance ("GMR") sensors, or the like. In at least some embodiments, the array of magnetic sensors are positioned within a block. In at least some embodiments, the medical device is a catheter (e.g., an electrophysiology ("EP") catheter, an intravascular ultrasound ("IVUS") catheter, or the like). In at least some embodiments, the medical device is a pill (e.g., an ingestible, insertable, or implantable pill for imaging, dispensing therapeutic drugs, or the like).

In at least some embodiments, the magnet is disposed in a housing. In at least some embodiments, the magnetic field is generated by one or more magnetic field windings. In at least some embodiments, the one or more magnetic field windings are physically coupled to the housing. In at least some embodiments, the one or more magnetic field windings are physically coupled to the medical device. In at least some embodiments, the one or more magnetic field windings are insertable into the patient. In at least some embodiments, the one or more magnetic field windings are external to the patient.

In at least some embodiments, the position and orientation system includes an array of magnetic field sensors that sense the magnetic field of the rotating magnet and a computer that computes the position and orientation of the rotating magnet from the sensed magnetic field data. In at least some embodiments, the position and orientation system is capable of sensing the position of the rotating magnet to within one mm center-to-center of the actual position of the rotating magnet. In at least some embodiments, the position and orientation system synchronously detects a specific rate of rotation of the rotating magnet. In at least some embodiments, the output of a miniature sensor that detects the angular position of the rotating magnet may be used as a reference for a lock-in amplifier that measures the sensed magnetic field of the rotating magnet. In at least some embodiments, the position and orientation of a plurality of rotating magnets each rotating at different frequencies may be concurrently obtained by the position and orientation system.

In at least some embodiments, the insertable medical device (e.g., an IVUS, an endoscope, a video pill, or the like) includes an imager (e.g., ultrasound, video, IR, UV, optical coherence tomography ("OCT"), Tissue Electrical Impedance, or the like). In at least some embodiments, when the insertable medical device includes an imager, imaging data from the imager may be merged with other imaging data from other imagers (e.g., x-ray, fluoroscope, CT, MRI, or the like) and with the position and orientation data to form composite images. In at least some embodiments, information from an electrocardiogram signal may be mapped out along patient vasculature (e.g., along walls of a patient's heart, or the like) and tracked using the position and orientation system.

FIG. 1 is a schematic side view of one embodiment of a patient 102 lying on a table 104. A medical device 106 is inserted into the patient 102. A rotating magnet 108 is disposed at a distal end of the medical device 106. A sensor head 110 is disposed external to the patient 102, while being in proximity to the patient 102. For example, in FIG. 1 the sensor head 110 is shown disposed under the table 104. The sensor head 110 receives signals that are transferred to a computer 112 which determines the position and orientation of the rotating magnet 108, via one or more sensor leads 114. In at least some embodiments, the sensor head 110 transmits signal data to the computer 112 via a wireless communication link. In at least some embodiments, one or more stator leads 116 interconnect the medical device 106 to a power source to generate a magnetic field which causes the rotation of the magnet 108 and which is sensed by the sensor head 110. In at least some embodiments, the one or more stator conductors 116 interconnect the medical device 106 to the computer 112. In at least some embodiments, the leads 116 include leads from a miniature sensor that measures the orientation of the rotating magnet 108.

Figure 2:
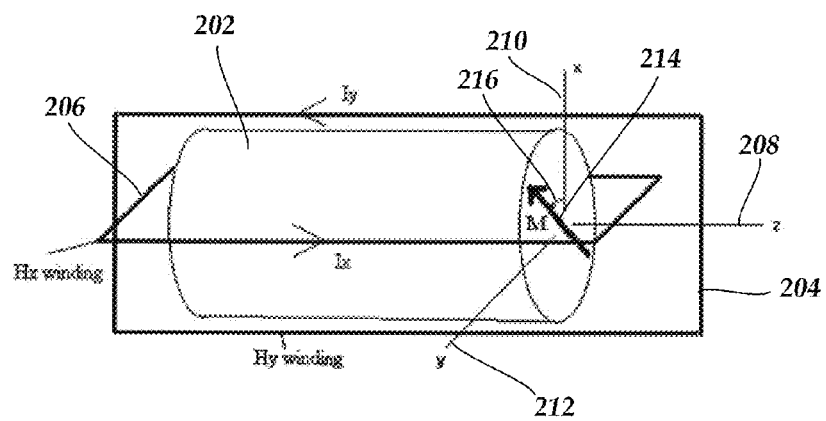
FIG. 2 is a schematic perspective view of one embodiment of a rotating magnet and associated magnetic field windings suitable for disposing in the medical device of FIG. 1, according to the invention.

FIG. 2 is a schematic perspective view of one embodiment of an exemplary rotatable magnet 202 and associated magnetic field windings ("windings"), represented as orthogonal rectangular boxes 204 and 206. Although the windings 204 and 206 are shown as two orthogonal rectangles, it will be understood that the each of the windings 204 and 206 may represent multiple turns of wire. When the windings 204 and 206 are spread out, a band of current may be generated instead of the lines of current shown in FIG. 2. It will also be understood that, as discussed below, there may be other numbers of windings. Additionally, it will be understood that the windings need not be orthogonal to one another.

The magnet 202 has a longitudinal (z) axis 208 about which the magnet 202 rotates. In order for the magnet 202 to rotate about the longitudinal axis 208, the torque must be about the longitudinal axis 208. Therefore, the magnetic field generated by the windings 204 and 206 must lie in a plane perpendicular to the longitudinal axis 208 with a magnetic field vector H for the windings 204 and 206 rotating about the longitudinal (z) axis 208 to torque and rotate the magnet 202. FIG. 2 also shows an x-axis 210 and a y-axis 212 that are orthogonal to each other and to the longitudinal axis 208. As shown in FIG. 2, the magnetization vector M 214 of the magnet 202 is in an x-y plane that is perpendicular to the longitudinal axis 208. The winding 204 produces a magnetic field at the center of the winding 204 that is parallel to the y-axis 212. The winding 206 produces a magnetic field at the center of the winding 206 that is parallel to the x-axis 210.

The magnet 202 may be formed from many different magnetic materials suitable for implantation including, for example, neodymium-iron-boron, or the like. One example of a suitable neodymium-iron-boron magnet is available through Hitachi Metals America Ltd, San Jose, Calif.

In at least some embodiments, the magnet 202 is cylindrical. In at least some embodiments, the magnet 202 is spherical. In at least some embodiments, the magnet 202 is radially symmetric, having an outside radius that varies along the length of the magnet. In at least some embodiments, the magnet 202 has a magnetization M of no less than 1.4 T. In at least some embodiments, the magnet 202 has a magnetization M of no less than 1.5 T. In at least some embodiments, the magnet 202 has a magnetization M of no less than 1.6 T. In at least some embodiments, the magnet 202 has a magnetization vector that is perpendicular to the longitudinal axis of the magnet 202.

In at least some embodiments, the magnet 202 is disposed in a housing. In at least some embodiments, the housing is hermetically sealed. In at least some embodiments, the housing is cylindrical. In at least some embodiments, the housing has a diameter that is no greater than 1.2 mm. In at least some embodiments, the housing has a diameter that is no greater than 1.1 mm. In at least some embodiments, the housing has a diameter that is no greater than 1 mm. In at least some embodiments, the housing has a diameter that is no greater than 0.9 mm. In at least some embodiments, the housing has a diameter that is no greater than 0.8 mm. In at least some embodiments, the housing is no longer than 8 mm. In at least some embodiments, the housing is no longer than 7 mm. In at least some embodiments, the housing is no longer than 6 mm. In at least some embodiments, the housing is no longer than 5 mm. In at least some embodiments, the housing is no longer than 4 mm.

In at least some embodiments, the diameter of the magnet 202 is no greater than 1.1 mm. In at least some embodiments, the diameter of the magnet 202 is no greater than 1 mm. In at least some embodiments, the diameter of the magnet 202 is no greater than 0.9 mm. In at least some embodiments, the diameter of the magnet 202 is no greater than 0.8 mm. In at least some embodiments, the diameter of the magnet 202 is no greater than 0.7 mm. In at least some embodiments, the longitudinal length of the magnet 202 is no greater than 7 mm. In at least some embodiments, the longitudinal length of the magnet 202 is no greater than 6 mm. In at least some embodiments, the longitudinal length of the magnet 202 is no greater than 5 mm. In at least some embodiments, the longitudinal length of the magnet 202 is no greater than 4 mm.

In at least some embodiments, the windings 204 and 206 provide a constant torque to rotate the magnet 202 at a constant frequency. In at least some embodiments, the magnet 202 rotates at a frequency of at least 20 Hz. In at least some embodiments, the magnet 202 rotates at a frequency of at least 30 Hz. In at least some embodiments, the magnet 202 rotates at a frequency of at least 50 Hz. In at least some embodiments, the magnet 202 rotates at a frequency of at least 100 Hz. In at least some embodiments, the magnet 202 rotates at a frequency of at least 500 Hz. In at least some embodiments, the magnet 202 rotates at a frequency of at least 1000 Hz. In at least some embodiments, the magnet 202 rotates at a frequency of at least 1500 Hz. In at least some embodiments, the magnet 202 rotates at a frequency of at least 2000 Hz. In at least some embodiments, the magnet 202 rotates at a frequency of at least 2500 Hz. In at least some embodiments, the magnet 202 rotates at a frequency of at least 3000 Hz.

In at least some embodiments, the magnet 202 rotates at a frequency that is no less than 20 Hz and no greater than 50 Hz. In at least some embodiments, the magnet 202 rotates at a frequency that is no less than 30 Hz and no greater than 100 Hz. In at least some embodiments, the magnet 202 rotates at a frequency that is no less than 30 Hz and no greater than 1000 Hz. In at least some embodiments, the magnet 202 rotates at a frequency that is no less than 500 Hz and no greater than 2000 Hz. In at least some embodiments, the magnet 202 rotates at a frequency that is no less than 500 Hz and no greater than 2500 Hz. In at least some embodiments, the magnet 202 rotates at a frequency that is no less than 500 Hz and no greater than 3000 Hz.

In at least some embodiments, the magnet 202 rotates at a frequency that is no less than 400 Hz and no greater than 700 Hz. In at least some embodiments, the magnet 202 rotates at a frequency that is no less than 400 Hz and no greater than 600 Hz. In at least some embodiments, the magnet 202 rotates at a frequency that is no less than 400 Hz and no greater than 500 Hz. In at least some embodiments, the magnet 202 rotates at a frequency that is no less than 500 Hz and no greater than 700 Hz. In at least some embodiments, the magnet 202 rotates at a frequency that is no less than 500 Hz and no greater than 600 Hz. In at least some embodiments, the magnet 202 rotates at a frequency that is no less than 600 Hz and no greater than 700 Hz.

In at least some embodiments, the windings are disposed on the medical device upon which the magnet is disposed. In at least some embodiments, the windings are disposed over the magnet. In at least some embodiments, the winding are disposed on, in, or around a housing in which the magnet is disposed.

It will be understood that there are many different multiple-phase winding geometries and current configurations that may be employed to form a rotating magnetic field. For example, a motor may include, for example, a two-phase winding, a three-phase winding, a four-phase winding, a five-phase winding, or more multiple-phase winding geometries. It will be understood that a motor may include many other multiple-phase winding geometries. In a two-phase winding geometry, as discussed above, the currents in the two windings are out of phase by 90°. For a three-phase winding, there are three lines of sinusoidal current that are out of phase by zero, 120°, and 240°, with the three current lines also spaced by 120°, resulting in a uniformly rotating magnetic field that can drive a cylindrical motor magnet magnetized perpendicular to the current lines.

Typically, the generated magnetic field is uniform. In at least some embodiments, however, the generated magnetic field is not uniform. For example, in at least some embodiments a single magnetic field winding may be employed to rotate the magnet. In at least some embodiments, a single wire is disposed adjacent one side of the magnet, with a return lead disposed away from the magnet.

Figure 3A:
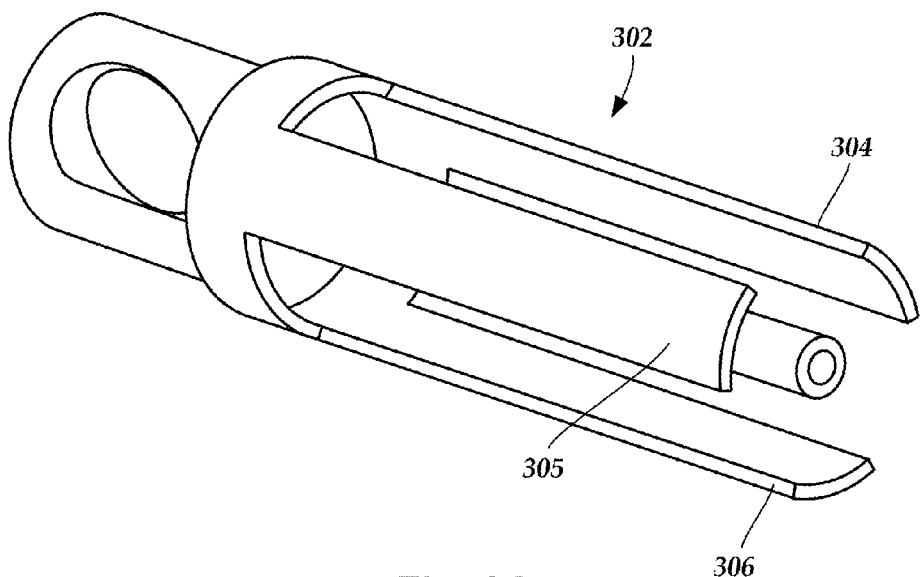
FIG. 3A is a schematic perspective view of one embodiment of a three-phase winding geometry configured and arranged for forming a rotating magnetic field around a magnet, according to the invention.

FIG. 3A is a schematic perspective view of one embodiment of a three-phase winding geometry 302 configured and arranged for forming a rotating magnetic field around a magnet (see e.g., 202 in FIG. 2). The three-phase winding 302 includes three windings, or lines of current, 304-306. In at least some embodiments, multiple windings may occupy a single layer on a cylindrical surface with no cross-overs. In FIG. 3A, windings 304-306 are shown as being single layer windings. In at least some embodiments, the windings 304-306 are free standing metal strips cut from the surface of a metal cylinder. In other embodiments, single layer windings or strips may be deposited on a non-conductive cylindrical surface. Such a winding may occupy a minimal volume in an insertable medical device. Although other geometries may also form a rotating magnetic field, the three-phase geometry 302 may have the advantages of allowing for a more compact motor construction than other geometries that require multiple turns with cross-overs that add to the radial dimension of the motor.

One useful property of a three-phase winding geometry 302 is that only two of the three lines 304-306 needs to be driven, while the third line is a common return that mathematically is equal to the third phase of current. This can be verified by noting that:

$$\sin(\omega t)+\sin(\omega t+120°)=-\sin(\omega t+240°)$$

For a three-phase winding geometry 302, current is driven into two lines with the zero and 120° phase shift of the two terms on the left side of this identity. The sum of the two terms returns on the common line with exactly the correct 240° phase shift on the right side of this equation needed to create the rotating magnetic field. It will be understood that the minus sign indicates that the return current is in the opposite direction of driven current.

In at least some embodiments, the three unsupported lines 304-306 may be supported by a substrate to increase mechanical stability. In at least some embodiments, the lines 304-306 are constructed from a solid metal tube, leaving most of the metal intact, and removing only metal needed to prevent shorting of the lines 304-306. In at least some embodiments, the removed portions are backfilled with a non-conductive material. In at least some embodiments, the lines 304-306 each have an overall wall thickness of no greater than 60 μm. In at least some embodiments, the lines 304-306 each have an overall wall thickness of no greater than 50 μm. In at least some embodiments, the lines 304-306 each have an overall wall thickness of no greater than 40 μm.

Figure 3B:
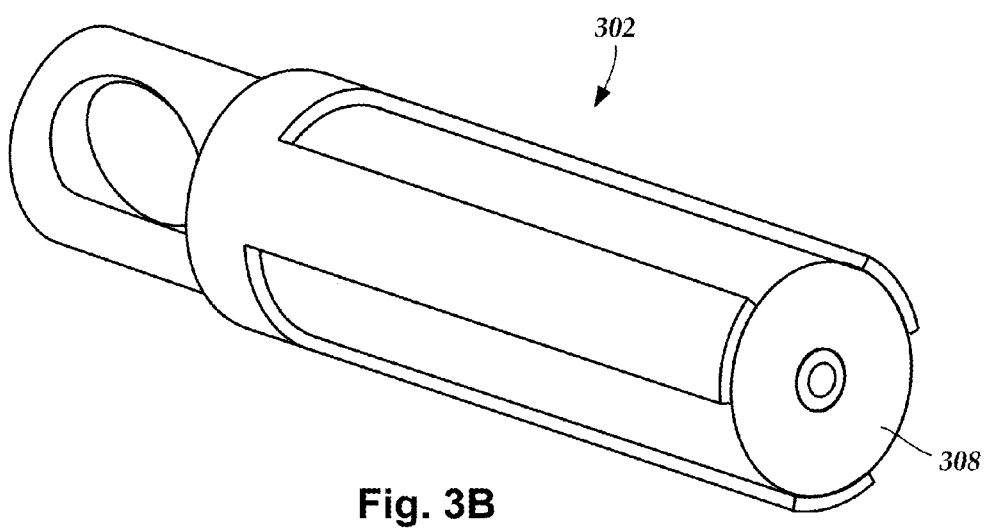
FIG. 3B is a schematic perspective view of one embodiment of a magnet disposed in the three-phase winding of FIG. 3A, according to the invention.
Figure 3C:
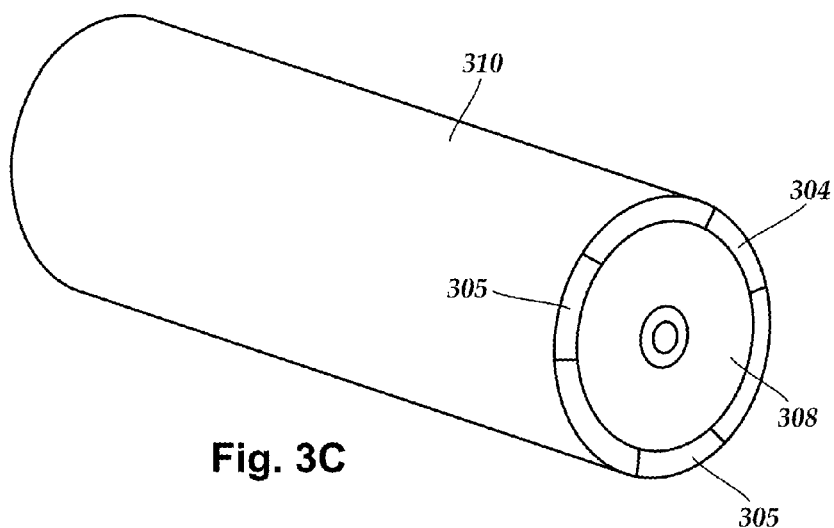
FIG. 3C is a schematic perspective transverse cross-sectional view of one embodiment of the three-phase winding and magnet of FIG. 3B disposed in a housing, according to the invention.
Figure 3D:
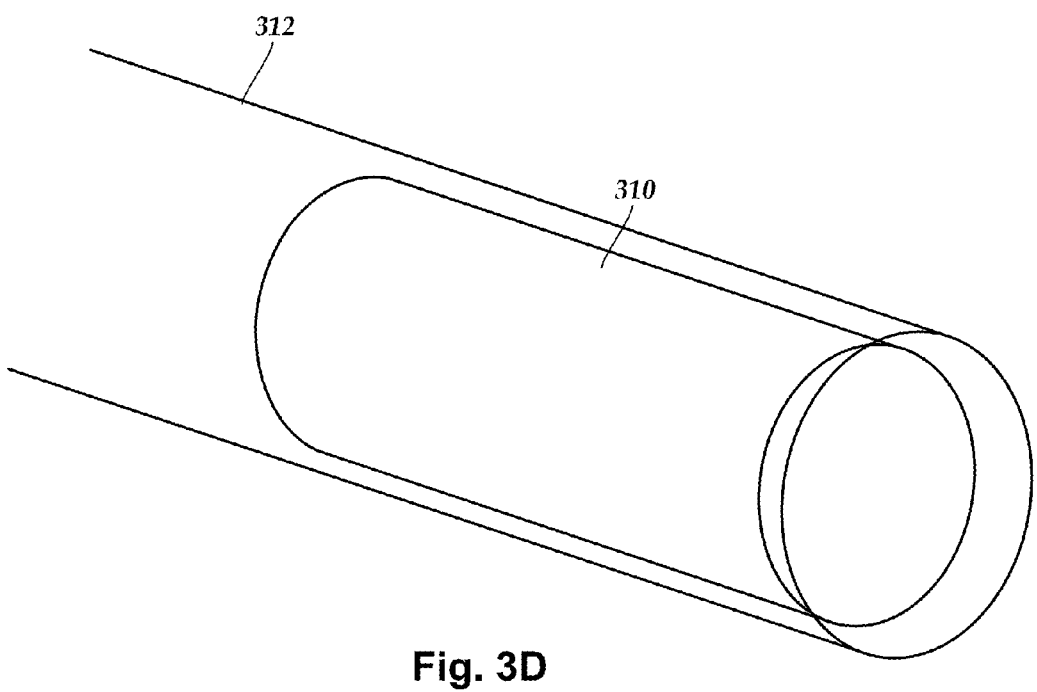
FIG. 3D is a schematic perspective view of one embodiment of the magnet, three-phase winding, and housing of FIG. 3C disposed in a distal end of a catheter, according to the invention.

FIG. 3B is a schematic perspective view of one embodiment of a magnet 308 disposed in the three-phase winding 302. FIG. 3C is a schematic perspective transverse cross-sectional view of one embodiment of the magnet 308 disposed in a housing 310. In FIG. 3C, the three-phase winding 302 is embedded in the housing 310. In at least some embodiments, the three-phase winding 302 is disposed within the housing 310. In at least some embodiments, the three-phase winding is disposed over the housing 310. FIG. 3D is a schematic perspective view of one embodiment of the housing 310 disposed at a distal end of a medical device 312 configured and arranged for insertion into a patient. In at least some embodiments, the medical device 312 is a catheter.

A spinning magnet generates a rotating magnetic field at points in the space surrounding the magnet. The strength of the magnetic field may be approximately half of the magnet's magnetization at the surface of the magnet, and decreases with the cube of the distance from the spinning magnet. In at least some embodiments, the position and orientation system includes an array of magnetic sensors positioned outside the patient that synchronously detects the magnetic field created by the magnet as the magnet rotates. In at least some embodiments, the currents driving the rotating magnet may be used as a reference to provide high resolution measurements. There are many ways to sense a magnetic field. A coil of wire can sense AC magnetic fields. The sensitivity, or signal to noise ratio, of the induction coil increases with the coil volume. Thus, large coils can be more sensitive than relatively smaller coils. If compact, small-volume sensors are desired for a given application, then modern sensors, such as the GMR sensors, may increase sensitivity. In at least some embodiments, six GMR magnetic sensors are placed at the corners of a block. In at least some embodiments, the block has sides measuring no more than four inches (approximately 10 cm) on a side.

The magnetic gradient tensor is measured and inverted using a known algorithm to produce the Cartesian coordinates and orientation of the rotating magnet. Without wishing to be held to any particular values, calculations using commercially available magnetic field sensors show that a location of a magnet may be localized to sub-millimeter accuracy when the rotating magnet has an 0.8 mm diameter and a 5 mm length and an array of magnetic sensors is located up to 0.5 meters from the rotating magnet. The accuracy may be improved using many different techniques including, for example, increasing the size of the rotating magnet, increasing the saturation magnetization of the magnet material, increasing the speed of the rotation of the magnet, increasing the interval over which data are averaged (i.e., reducing the sampling rate), increasing the volume of the sensors, increasing the sensitivity of the sensors, reducing the distance between the rotating magnet and the sensor array, increasing the number of magnetic sensors, improving the relative locations of the sensors in the sensor array, sensing the angular position of the magnet as it rotates and providing this data as a reference for a lock in amplifier whose input is a magnetic field sensor, or the like or combinations thereof.

Figure 4:
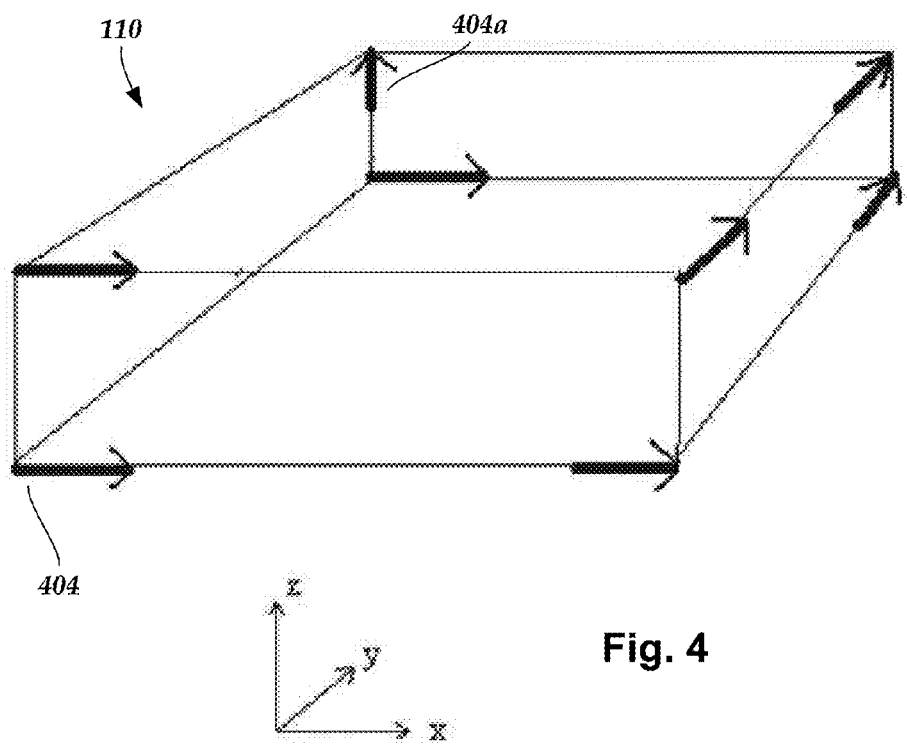
FIG. 4 is a schematic perspective view of one embodiment of a sensor head of the position and orientation system of FIG. 1, according to the invention.

FIG. 4 is a schematic perspective view of one embodiment of the sensor head 110 for a position and orientation sensor. In at least some embodiments, the sensor head 110 is disposed externally from the patient. An array of magnetic sensors, such as magnetic sensor 404, synchronously detects the magnetic field generated by the rotation of the magnet 308. Each of the arrows represents a miniature magnetic sensor 404 configured and arranged to measure a component of a magnetic field in the direction of the arrow. In at least some embodiments, multiple sensing heads may be used if more range or more accuracy is needed.

In at least some embodiments, gradient tensor components are measured as the difference between pairs of magnetic field sensor outputs divided by the distance between the magnetic field sensors 404. In at least some embodiments, unpaired magnetic field sensors, such as 404a, may be used to correct the measured gradients for misalignment. Correction coefficients may be determined by performing a one-time calibration procedure.

In at least some embodiments, the magnetic field sensors 404 are GMR magnetic field sensors. Currents driving the rotation of the magnet 308 may be used as a reference to provide high resolution measurements. Alternatively, a small sensor adjacent magnet 308 may measure its angular position. The measured angular position may be used as a reference to provide even higher resolution measurements. In at least some embodiments, the sensor head 110 is machined from a hard plastic.

As shown in FIG. 3D, in at least some embodiments the rotating magnet 308 is disposed on, or within, a catheter 312, such as an electrophysiology ("EP") catheter or an intravascular ultrasound ("IVUS") catheter. In at least some embodiments, the catheter 312 may be used to construct an anatomical map of a heart chamber by touching the chamber walls at a number of points, computing the location of each point in three dimensional space, and mathematically interpolating between points to form an image of the chamber wall. An electro-anatomical map may be obtained by measuring at least one of the amplitude or timing of an electrocardiogram signal measured at an electrode of the EP catheter. In at least some embodiments, the measurements may be displayed, for example, as a color coded image, in conjunction with the anatomical map. Once mapped, the present position of the catheter 312 may be displayed on the map and tracked, which may reduce use of fluoroscopy to guide the EP catheter 312. Mapping one or more anatomical structures (e.g., the walls of a heart chamber) may be used to identify sites of abnormal conduction or arrhythmic foci, which may then be treated, for example, by ablation.

As discussed above, in at least some embodiments the position and orientation system is designed to achieve sub-millimeter localization accuracy while utilizing a rotating magnet housing 310 that is small enough to fit within the distal end of a catheter 312, such as an EP catheter, an IVUS catheter, or the like. An inversion algorithm can solve for the vector position and angular orientation of the rotating dipole magnet. An estimate of localization accuracy can be obtained by considering the simple case of a single magnetic sensor located at a distance, r, from a magnetic dipole along the direction of its magnetization vector. The magnetic field in this case is given by:

$$B = m/(2\pi r^3); \qquad (1)$$

where B=magnetic field in Tesla; m=magnet's magnetic moment in Tesla-m$^3$; and r=distance from magnet measured along its magnetization direction.

Eq.(1) may be inverted to solve for the distance "r" given the measurement of B and the known value of the magnetic moment "m." To find localization accuracy, assume that the sensor resolution (peak noise) is $\delta B$. The resolution of the distance determination is obtained by differentiating Eq.(1):

$$\delta r/r = \delta B/(3B); \qquad (2)$$

with $\delta r$ preferably less than one mm. For a concrete example, assume that r=0.5 m or about 20", intended to represent a maximum distance between a catheter tip in a patient's heart and a sensor under the patient table (see e.g., FIG. 1). The magnetic field B at this distance is computed from Eq.(1) by noting that:

$$m = MV; \qquad (3)$$

where M=magnet magnetization in Tesla; and V=magnet volume in m$^3$.

Modern neodymium-iron-boron magnets have M as high as 1.5 Tesla. Without wishing to be bound by any particular values, when the overall diameter of the housing is 1 mm, and the thickness of the windings is 0.05 mm, the gap between the magnet 308 and the windings 302 is taken as approximately 0.05 mm, yielding a magnet diameter of 0.81 mm. With the magnet rotor length of 5 mm, the magnetic moment of Eq.(3) is m=3.9×10$^{-9}$ T-m$^3$, and the field at 0.5 m from Eq.(1) is B=4.9×10$^{-9}$ Tesla.

To compute the magnetic field sensor noise, consider a specific commercially available magnetic field sensor, the HMCI001 giant magnetoresistance ("GMR") sensor (available as an integrated circuit measuring 12.8×7.5×2.5 mm) available from Honeywell International, Morris Township, N.J. The rms value of the magnetic field white noise in a one-Hz bandwidth for this sensor is 2.4×10$^{-11}$ Tesla. For the rotating magnet 308, it may be assumed that the sensor data can be band-pass filtered in a one Hz band pass around the precisely known rotation frequency. For specificity, one can take the rotation rate to be 500 Hz, which is in the white noise region of the Honeywell GMR sensor, and average the data over ten cycles, so that the output data rate is 50 Hz, which is adequate for EP mapping. The averaging reduces the noise by the square root of ten. The peak value of the noise is then: $\delta B = 1.1 \times 10^{-11}$ Tesla. Solving Equation (2) for the localization resolution gives: $\delta r = 0.4$ mm.

The localization resolution of $\delta r = 0.4$ mm may be improved by, for example, increasing the magnet rotation rate, reducing the band pass, reducing the sampling rate, increasing the size of the magnet, using a more accurate magnetic sensor, or increasing the number of independent sensors that measure the magnetic field of the rotor. These factors may be traded off, for example, to utilize a smaller rotating magnet package.

In practice, a certain amount of magnetic field interference may be present in the surroundings. The amount of magnetic field interference may be reduced by choosing the precise magnet rotation frequency at a quiet spot in the noise spectrum. It is common practice, however, to cancel the noise to first order by using pairs of magnetic field sensors in a gradiometer configuration. Magnetic field sensors may be organized in a gradiometer array pattern to yield a measurement of the magnetic gradient tensor, G. The tensor elements are given by:

$$G_{ij} = \partial B_i / \partial r_j; \qquad (4)$$

where $G_{ij}$=i,j element of the gradient tensor in Tesla/m and i,j=1 to 3; Bi=the i component of the magnetic field i=x,y,z, in Tesla; and $r_i$=i component of the position vector=x,y,z in meters.

The gradient components can be measured as the finite difference between the outputs of two magnetic field sensors divided by the sensor separation in meters. It can be shown that if the gradiometer tensor is measured in free space (free of electric currents and magnetic materials), then it is traceless and symmetric, and is defined by five components: $G_{x,x}$, $G_{x,y}$, $G_{x,z}$, $G_{y,y}$, and $G_{y,z}$. It has been shown that the gradiometer tensor may be inverted to find the Cartesian coordinates and orientation angles of a magnetic dipole.

The five independent gradient components may be measured by magnetic field sensors at the corners of a rectangular block. As show in FIG. 4, the magnetic field sensors 404 are disposed in a rectangular block 110. The arrows shown in FIG. 4 represent magnetic field sensors oriented along the direction of the arrows, and the gradient tensor components are taken as differences between pairs of magnetic field sensor outputs divided by the distance between the magnetic field sensor pair.

In practice, the magnetic field sensors 404 may not be perfectly aligned. Any misalignment, however, may produce a correction to the true gradient that is proportional to the three components of the measured magnetic field. Thus, a correction tensor may be formed whose elements are sums of the magnetic field components with coefficients determined in a calibration procedure.

As one example, using the inversion algorithm at time points sampled at a rate that is a multiple of the rotation rate can produce orientation vectors that rotate in time at a known frequency. The measurements may be averaged at the desired data rate, and the vector perpendicular to all measured vectors (i.e., the vector through the magnet axis) may be determined.

Multiple catheters may be constructed with identical rotating magnets that rotate at distinctly separate frequencies. The magnetic sensor outputs may be filtered at each of these frequencies to localize the multiple catheters simultaneously.

Many sensor arrays are possible, in addition to the tensor array of FIG. 4. A minimum of five independent magnetic field measurements are needed to find the three Cartesian coordinates and two orientation angles of the rotor magnet. More redundant sensor outputs may be combined to improve the measurement accuracy.

There are many mathematical approaches to inversion of an array of sensor data. One simplification is to note that during one revolution of the rotor (e.g., 1/500 sec at 500 Hz), the position of the distal end of a catheter upon which a rotating magnet is disposed cannot change appreciably. If many magnetic field data samples are collected in a revolution, the assumption that the Cartesian coordinates are the same for all of these samples, simplifies and linearizes the solution for the components of the magnetic moment vector (orientation angles). This data may be combined to solve for the vector that is perpendicular to all of the moment vectors, namely the vector defining a longitudinal axis of the catheter.

As discussed above, in at least some embodiments a three-axis position and a three-axis orientation of the rotating magnet 308 disposed at a distal end of an EP catheter 312 may be obtained with reference to one or more GMR magnetic field sensors 404 attached to the catheterization laboratory table 104. In at least some embodiments, a rotating magnet may be disposed on one or more medical devices inserted into a patient's heart to measure the position of the inserted medical devices with reference to the GMR magnetic field sensors 404.

In at least some embodiments, in addition to a rotating magnet disposed on a medical device disposed in a patient, one or more additional rotating magnets may be disposed at one or more locations on a fluoroscope to locate the positioning of the fluoroscope, or other external imaging device with reference to the GMR magnetic field sensors 404 so that the positioning of one or more inserted medical devices may be accurately registered to the position of the imager components. This may enable merging actual locations of multiple medical devices into a 3-D picture of a region of the patient, such as patient vasculature or heart chamber.

In at least some embodiments, a rotating magnet may be disposed on a calibration frame to calibrate sensing measurements. The calibration frame may be temporarily positioned on the table 304 on which the patient 102 is disposed at the location where, for example, the patient's heart would be located.

In at least some embodiments, the rotating magnet 308 may be disposed on a distal end of an IVUS catheter 312. In at least some embodiments, the rotating magnet 308 may be utilized as a motor to drive the rotation of a transducer (or a mirror) during ultrasound imaging, and also utilized to make use of the spinning magnetic field created by the rotating magnet 308 to map the location and orientation of the catheter 312 with respect to magnetic sensors 404 positioned external (and in proximity) to the patient 102, for example, positioned on the catheterization laboratory table 104 on which the patient 102 is disposed. Thus, 3-D location and motion of the catheter 312 may be sensed accurately without needing pullback sensing, such as fluoroscopy, thereby reducing patient (and health care professional) exposure to potentially harmful radiation.

In at least some embodiments, the measurements may be associated with electrocardiogram data to enable visualization of the repeated motion of patient vasculature (e.g., walls of the patient's heart, or the like) during the cardiac cycle. This may provide a true moving 3-D image of the ultrasonically-derived dimensions of, for example, the inside of the heart chambers. In at least some embodiments, these measurements may then be accurately registered with other images, such as scans from a CT, x-ray, MRI, or the like, if markers were placed on the patient during these scans, or if anatomical features of the patient are used as markers.

In at least some embodiments, various medical image data may be merged during the medical procedure to generate a more accurate moving 3-D picture of the region of the body before and after each step of a medical procedure, and record a map of the actual treatment performed at each location.

In at least some embodiments, the rotating magnet may be disposed in an endoscope. In at least some embodiments, endoscopy provides a live video picture of an internal portion of a patient. By adding a position and orientation system to a rotating magnet disposed on an endoscope, a medical professional may generate a map of a patient's colon or other structure and move around the map using computer analysis of the data to visualize where suspicious sites are located. Return to the suspicious site(s) under robot control (or guided human control) would also be possible.

In at least some embodiments, the rotating magnet 308 may be coupled to a mirror that reflects a beam of ultrasound or optical energy into adjacent tissue. The beam may be reflected back from the tissue to form an image of an annular region of tissue surrounding the device. Both IVUS and OCT beams can penetrate to a depth into the tissue, thus the reflected beam may be resolved in time to provide a two-dimensional image of the surrounding tissue. The rotating magnet enables the image acquisition while simultaneously providing the rotating magnetic field for device localization.

In at least some embodiments, the rotating magnet 308 may be used to locate the catheter 312 as the catheter 312 is used for an examination of a patient's gut cavity, resulting in an even less invasive laparoscopy. If the catheter is steerable by external controls, the location of the catheter 312 can be located and integrated with, for example, video data produced by a flexible fiber optic bundle carried by the steerable catheter 312.

In at least some embodiments, the rotating magnet 308 may be used in conjunction with transvascular devices that utilize a guide wire. The magnetic navigation method may find use when it is necessary to access a cavity, such as the chambers of the heart, abdomen, or the like. In at least some embodiments, a rotating magnet 308 may be integrated into the tip of a guidewire to locate the tip on a previously-acquired fluoroscopic map of an arterial bed, such as a coronary artery, peripheral artery, or the like. After the initial map is obtained, the localization system may be used instead of fluoroscopy to display the guidewire tip location on the map, thus limiting patient (and health care professional) x-ray exposure.

In at least some embodiments, the rotating magnet 308 may be used to improve accuracy determination of the end effector of a multi-axis robot device. Current methods include accurately measuring the angle of each joint and calculating the probable location of the tip of the end effector. Errors, however, may accumulate to make sub-millimeter end effector position determination difficult. When the rotating magnet 308 is positioned on the end effector and the magnetic sensors 404 are positioned in proximity to the working region, then a more accurate positioning may be possible. This would be valuable for machining large devices with high tolerance requirements, such as the propellers of submarines.

In at least some embodiments, the rotating magnet 308 may be disposed into a pill or other device that is, when in use, entirely within a patient, such as an imaging pill, and used to enable navigation. In at least some embodiments, the rotating magnet 308 is small enough to be added to the pill package, and offers the ability to relay the location and orientation of the pill with each captured video picture. This will allow the creation of a 3-D image of the small intestine as the pill moves through the gut. In at least some embodiments, a mirror coupled to the rotating magnet 308 may reflect an optical or ultrasound beam into the tissue to form OCT or IVUS images of tissues beneath the surface of the body passage being imaged with conventional video.

In at least some embodiments, an external magnetic field may provide a translational force to magnet 308 to move the pill toward an object of interest identified in the video, or by an outside imaging device. If a marker device is placed on the body before the pill is swallowed, the image data created may be integrated with the pill video image and pill location, so the pill can be deflected toward an object identified in an earlier scan, such as a barium X-ray image.

Figure 5:
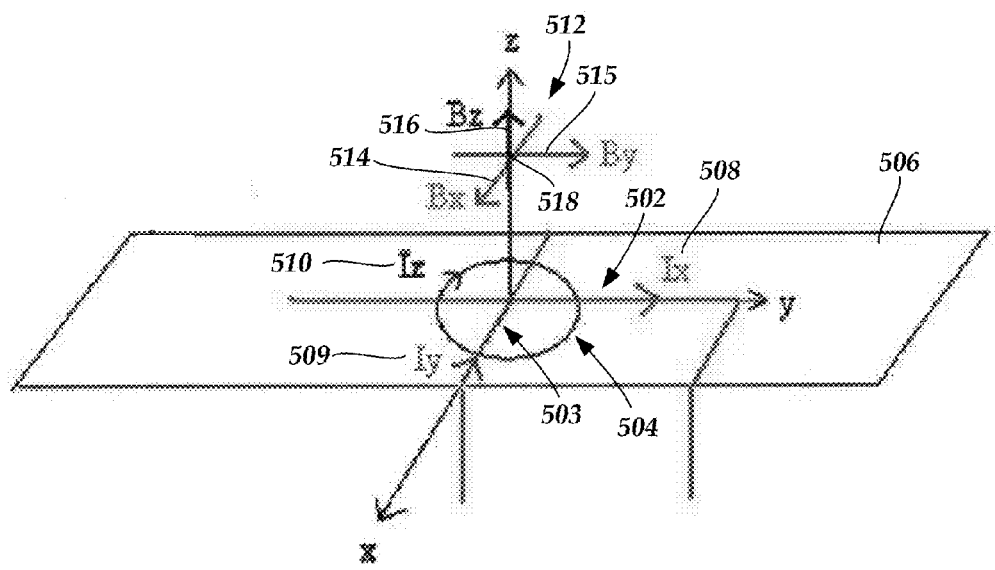
FIG. 5 is a schematic perspective view of one embodiment of portions of three orthogonal magnetic field windings positioned on a plane that form a magnetic field above the plane, according to the invention.

In at least some embodiments the windings are disposed external to the medical device onto which the magnet is disposed. In at least some embodiments the windings are disposed external to the patient into which the magnet is disposed (i.e., the windings are extracorporeal). The extracorporeal windings form a magnetic field within the patient at the location of the magnet within the patient. FIG. 5 is a schematic perspective view of one embodiment of portions of three orthogonal windings 502-504 positioned on a plane 506. Currents Ix 508, Iy 509, and Iz 510 transmit through the portions of the orthogonal windings 502-504, respectively, as shown by arrows. When currents 508-510 are transmitted through the windings 502-504 in the directions indicated, a magnetic field 512 is formed having three orthogonal components Bx 514, By 515, and Bz 516, respectively. In at least some embodiments, the intersection 518 represents a hypothetical location of a rotatable magnet (see e.g., 308 in FIG. 3) within a patient. In at least some embodiments, the portions of the windings 502 and 503 positioned on the plane 506 are straight. In at least some embodiments, the portion of the winding 504 positioned on the plane 506 is a circular loop.

In at least some embodiments, the plane 506 is positioned within a surface suitable for supporting a patient undergoing a medical procedure involving the insertion of a medical device into the patient. In at least some embodiments, the plane 506 is positioned above or below a surface suitable for supporting the patient. In at least some embodiments, the windings 502-504 are configured such that the magnetic field 512 is formed within the patient lying on the plane 506. In at least some embodiments, the magnetic field 512 has a constant amplitude.

Each of the portions of the orthogonal windings 502-504 positioned on the plane 506 includes a return path (not shown). The return paths of the windings 502-504 may be in any configuration. In preferred embodiments, the return paths are positioned away from the portions of the windings 502-504 positioned on the plane 506. It will be understood that each of the windings 502-504 represents one or more turns of a wire.

When the magnetic field 512 is formed at a height (z) above the plane 506, the magnetic field 512 is given by:

$$H_{x,y} = NI_{x,y}/(2\pi z); \text{ and}$$

$$H_z = NI_z/(D[1+(2z/D)^2]^{3/2});$$

where D is the diameter of the circular loop carrying current $I_z$. It will be understood that adjusting the currents $I_x$, $I_y$, and $I_z$ independently allows the above magnetic field components to take on any value. In particular, the magnetic field vector may be directed perpendicular to the axis of a magnet 308 located at point z. By varying the magnetic field components over time, the magnetic field may be rotated about the longitudinal axis of a magnet 308 located at point z, causing the magnet to rotate about its longitudinal axis.

In at least some embodiments, z is formed at a location such that the magnetic field is within a patient lying on a surface at, or adjacent to, the plane 506. For example, when a target magnet location is the patient's aorta, and when the patient is lying on a surface at, or adjacent to, the plane 506, z is no greater than 0.3 meters. In at least some embodiments, N=200 and $I_{x,y}$=3 amps. In at least some embodiments, the windings 502-504 are formed from stranded wire that forms a flexible band of current.

Figure 6:
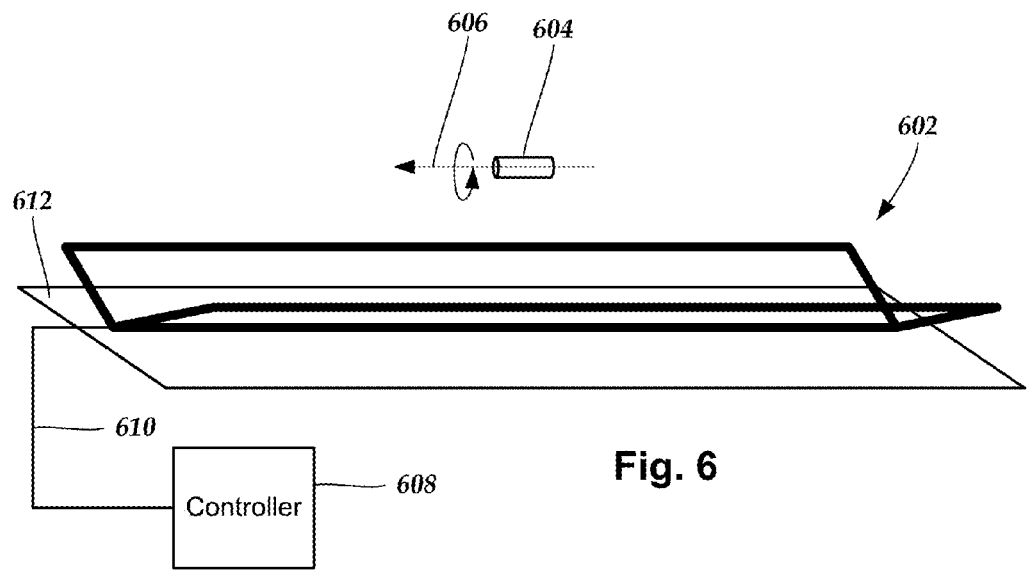
FIG. 6 is a schematic perspective view of one embodiment of a stator winding for driving a motor magnet, the stator winding disposed above a bed, according to the invention.

FIG. 6 is a schematic perspective view of one embodiment of a three-phase winding 602 generating a magnetic field that drives rotation of a motor magnet 604 around a longitudinal axis 606 of the magnet 604. A controller 608 is coupled to the three-phase winding 602 by one or more conductors 610. In at least some embodiments, the controller 608 provides power for generating the magnetic field. In FIG. 6, the three-phase winding 602 is shown disposed on a plane 612. In at least some embodiments, the plane 612 is a bed on which a patient may lie during a medical procedure involving the insertion of a medical device into the patient. In at least some embodiments, the three-phase winding 602 may be repositioned to allow patient access to the bed. In at least some embodiments, the three-phase winding 602 may be used by the patient as a bed railing, an arm rest, or the like during a procedure.

Figure 7:
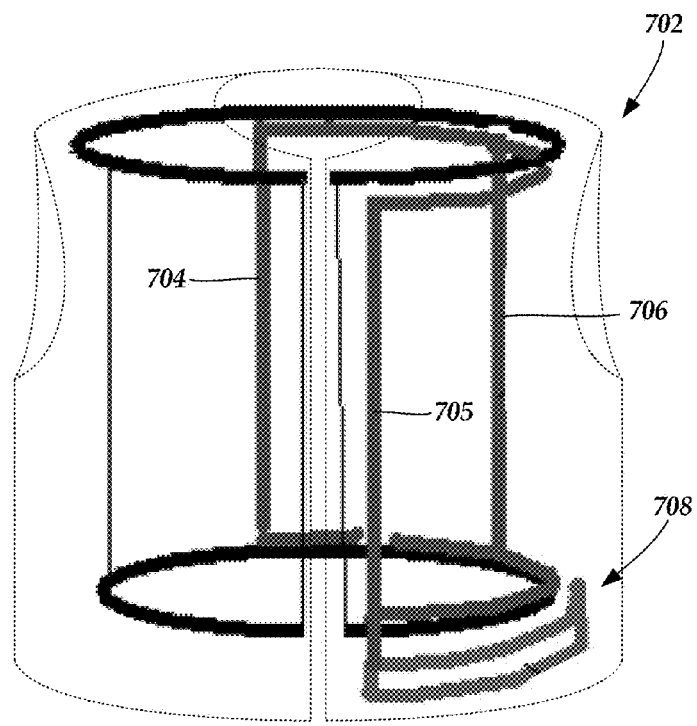
FIG. 7 is a schematic perspective view of one embodiment of a stator winding for driving a motor magnet, the stator winding disposed in a vest, according to the invention.

In alternate embodiments, the windings are disposed in a garment that may be worn by a patient. FIG. 7 is a schematic view of one embodiment of a vest 702 that may be worn by a patient. The vest 702 includes three-phase winding 704-706. In at least some embodiments, the vest 702 includes a controller 708 coupled to the vest 702. In at least some embodiments, the controller 708 includes an electronic subsystem for controlling one or more operations of the device 312, such as drive electronics and controls, transmit and receive electronics, and image processing and display electronics. In at least some embodiments, the controller 708 includes a power supply, such as one or more batteries. It will be understood that the three-phase winding 704-706 may be incorporated into many different types of garments besides vests including, for example, jackets, coats, sweaters, shirts, overalls, coveralls, robes, wraps, or the like.

As discussed above, in some embodiments the medical device is a pill (or seed, or the like) that may be ingested by (or inserted, or implanted into) a patient. Power for such a pill may be supplied by a battery, or be supplied externally to recharge a battery or capacitor, or to directly power the pill. The energy storage capacity of a battery of an imaging pill may not be sufficient to supply enough power to the pill in many (or multiple) applications, for example, simultaneous video and IVUS (or OCT) imaging.

In at least some embodiments, the pill includes a magnet configured and arranged to rotate freely within a housing. In at least some embodiments, the rotation of the magnet is driven by a magnetic field generated externally from the pill. In at least some embodiments, the rotation of the magnet is driven by a magnetic field generated externally from the patient. In at least some embodiments, the rotation of the magnet is driven by a magnetic field generated by external windings. The external magnetic field is sufficiently large to rotate the magnet. Power is generated in the windings of the pill by the close proximity of the windings to the rotating magnet. This power may be used in addition to, or as an alternative to, a battery.

Figure 8:
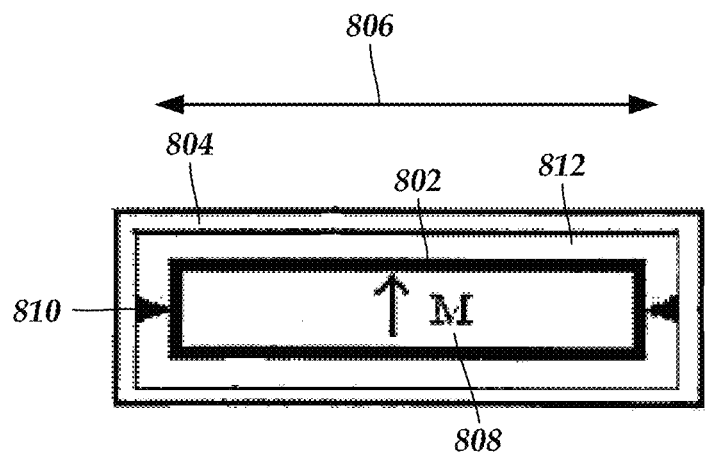
FIG. 8 is a schematic longitudinal cross-sectional view of one embodiment of a magnet disposed in a housing, according to the invention.

Many external winding arrangements may be configured to generate magnetic fields that rotate in a plane perpendicular to the longitudinal axis 806 of the magnet 802 (see e.g., FIG. 8). The external magnetic field may be supplied in many forms. For example, in alternate embodiments, instead of using external magnetic field windings, a second, larger rotating magnet may be placed outside the patient as close as possible to the pill.

In at least some embodiments, a user may wish to know the geometrical location and orientation of the pill at all times, for example, to enable better graphical displays and more accurate diagnoses. Conventional electromagnetic localizers typically generate an array of AC magnetic fields that are sensed by magnetic sensors within a device. The sensed signals are used to infer the device location and orientation. For applications in which the device is not tethered and moves freely within the body (e.g. an imaging pill), conventional localization may require telemetry of all sensor outputs at a very high data rate. By contrast, a rotating magnet rotates at a known frequency of the external rotating magnetic field. The magnetic field generated by the rotating magnet may be sensed by external magnetic sensors that are locked onto the particular rate of rotation of the magnet. Thus, the location and orientation of the magnet within the pill may be accurately determined, using only small and relatively inexpensive external field sensors, as discussed above with reference to FIG. 4.

In at least some embodiments, the rotation of the magnet may be used to generate power, via a power generation system, to application electronics. In at least some embodiments, the power generation system includes a rotating magnet, one or more layers of fine wire ("generator windings") surrounding the rotating magnet and configured and arranged to generate electricity when the magnet rotates. In at least some embodiments, the power generation system further includes an electronic subsystem that rectifies, filters, or stores the generated energy (or a combination of these functions). In at least some embodiments, the power generation system additionally includes one or more output leads that supply generated power to adjacent application electronics. Examples of applications include, for example, imaging, sensors, telemetry, drug delivery, tissue removal or repair, electrical stimulation, implantable device delivery, or the like or combinations thereof.

In at least some embodiments, power is generated in a wireless pill that is swallowed by a patient and that provides optical images of the gastro-intestinal tract as the pill moves through the gastro-intestinal tract. In at least some embodiments, the power generation system is smaller than a battery for a conventional imaging pill. Thus, by utilizing a power generation system to power associated electronics in lieu of a battery, there may be additional space within the pill. In at least some embodiments, the space may be filled with one or more sensors or one or more imaging devices, such as an IVUS imaging transducer, which may consist of a piezoelectric transducer that rotates with the generator magnet. Continuous input of electrical power may enable more electronics and sensors, and better and faster telemetry. In at least some embodiments, enough power may be externally generated to enable additional features to be included in the pill, such as miniature cutters, drug delivery systems, or the like.

In at least some embodiments, an externally generated rotating magnetic field may be used to change the orientation of the pill, or to translate the pill to a desired location. In at least some embodiments, the orientation of the pill may be adjusted by directing the plane of rotation of the externally generated magnetic field away from the plane of the rotating magnetization vector of magnet 604. Adjusting the plane of rotation places a torque on the pill that tends to align the plane of the rotating magnet magnetization vector with the plane of the external rotating field. In at least some embodiments, the pill may be translated by providing a rotating external magnetic field that increases in amplitude in the desired direction of translation.

FIG. 8 is a schematic longitudinal cross-sectional view of one embodiment of a magnet 802 disposed in a housing 804. In at least some embodiments, the housing 804 is non-magnetic and non-metallic, to increase the ability of the magnet 802 to couple to the externally generated magnetic field, and to the generator windings (902 in FIG. 9). The magnet 802 has a longitudinal axis 806 (shown in FIG. 8 as two-headed arrow). In at least some embodiments, the magnetization vector M 808 of the magnet 802 is perpendicular to the longitudinal axis 806. In at least some embodiments, the magnet 802 is configured and arranged to rotate on bearings 810. In at least some embodiments, the magnet 802 is configured and arranged to rotate on one or more fluids disposed in a gap 812 between the magnet 802 and the housing 804. In at least some embodiments, the one or more fluids include a ferrofluid.

Figure 9:
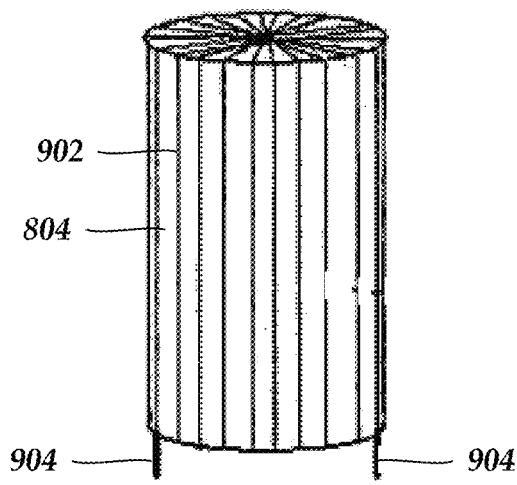
FIG. 9 is a schematic perspective view of one embodiment of magnetic field windings disposed over the housing of FIG. 8, according to the invention.

FIG. 9 is a schematic perspective view of one embodiment of generator windings 902 disposed on the housing 804 of the pill. In at least some embodiments, the generator windings 902 begin at a point called zero degrees and move laterally to 180 degrees, then back to form layers. One or more input leads 904 extend from the generator windings 902. In at least some embodiments, the housing 804 is cylindrical. In at least some embodiments, the generator windings 902 are disposed within the housing 804. In at least some embodiments, the generator windings 902 are disposed over the housing 804. In at least some embodiments, the generator windings 902 are embedded within the housing 804.

Figure 10:
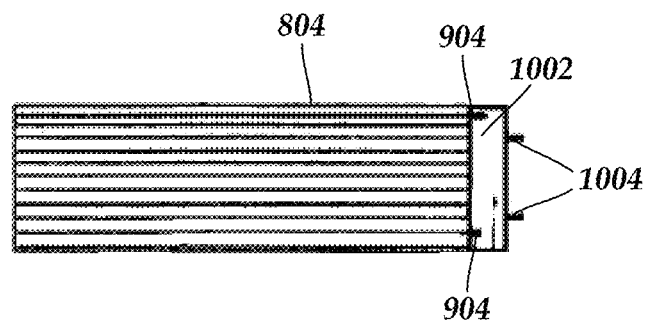
FIG. 10 is a schematic side view of one embodiment of an electronic subsystem coupled to the enclosure of FIG. 8, according to the invention.

In at least some embodiments, the generator windings 902 output power to an electronic subsystem that, in turn, outputs power to one or more electronic applications of the pill, such as providing imaging capabilities. FIG. 10 is a schematic side view of one embodiment of electronic subassembly 1002 coupled to the housing 804 such that the one or more input leads 904 couple to the electronic subassembly 1002. In at least some embodiments, the electronic subassembly 1002 also include one or more output leads 1004 for outputting power from the electronic subassembly 1002 to the application electronics.

Figure 11:
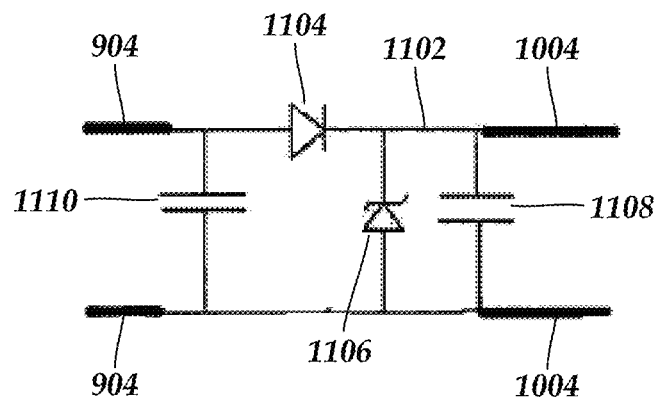
FIG. 11 is a schematic view of one embodiment of an electric circuit for the electronic subsystem of FIG. 10, according to the invention.

FIG. 11 is a schematic view of one embodiment of a diagram for an exemplary circuit 1102 of the electronic subassembly 1002. In at least some embodiments, the circuit 1102 includes a rectifier 1104 to convert AC power to DC power. In at least some embodiments, the circuit 1102 includes a voltage regulator 1106. In at least some embodiments, the circuit 1102 includes a filter/storage capacitor 1108. In at least some embodiments, the circuit 1102 includes a tuning capacitor 1110.

In at least some embodiments, the electronic subassembly 1002 further includes a rechargeable battery. Using a rechargeable battery may relieve the requirement of continuously supplying external power. In at least some embodiments, the electronics 1002 includes a microprocessor to monitor the charging process. In at least some embodiments, the electronics 1002 includes a telemetry unit to provide power status to the user.

As discussed above, an externally applied magnetic field causes rotation of the magnet 802 in a plane perpendicular to the longitudinal axis 806 of the magnet 802. While means are suggested to enable this, an alternative approach is to form a spherical magnet that is free to rotate within a spherical housing. The spherical magnet has no preferred axis, and its magnetic moment will automatically align to any externally applied field direction. To optimally extract power from the rotating spherical magnet, three orthogonal generator windings may be used to gather power independent of the plane of rotation of the spherical magnet.

Figure 12:
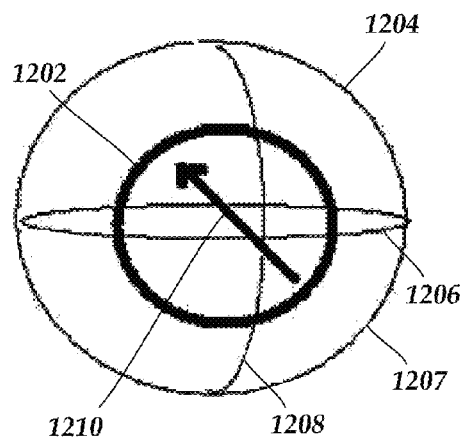
FIG. 12 is a schematic side view of one embodiment of a spherical magnet disposed in a spherical housing, according to the invention.

FIG. 12 is a schematic side view of one embodiment of a spherical magnet 1202 disposed in a spherical housing 1204 on which orthogonal generator windings 1206-1208 are disposed. In at least some embodiments, the spherical magnet 1202 is free to rotate within the spherical housing 1204. In at least some embodiments, the spherical magnet 1202 has no preferred axis, and its magnetic moment 1210 (shown in FIG. 12 as an arrow) will automatically align to any externally applied magnetic field direction. To optimally extract power from the rotating sphere, the generator windings 1206-1208 may be used to gather power independent of the plane of rotation of the spherical magnet 1202.

Figure 13:
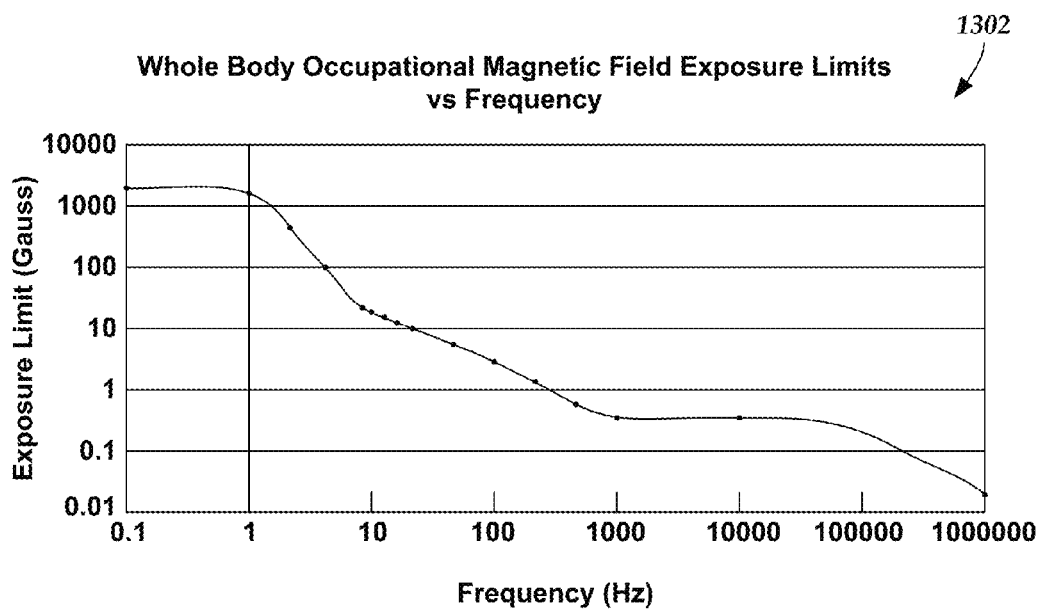
FIG. 13 is one embodiment of a graph of magnetic field exposure limits versus frequency, according to the invention.

While RF energy is a conventional modality for wireless power, it has some limitations. For example, magnetic field exposure limits fall off with increasing frequency into the RF range. FIG. 13 is a schematic graph 1302 of magnetic field exposure limits versus frequency. As shown in FIG. 13, the magnetic field exposure limit decreases as the frequency increases. In at least some embodiments, the power generation system takes advantage of the higher exposure limits by operating at lower frequencies.

In at least some embodiments, the power generation system operates at a frequency that is no greater than 500 Hz. In at least some embodiments, the power generation system operates at a frequency that is no greater than 400 Hz. In at least some embodiments, the power generation system operates at a frequency that is no greater than 300 Hz. In at least some embodiments, the power generation system operates at a frequency that is no greater than 200 Hz. In at least some embodiments, the power generation system operates at a frequency that is no greater than 100 Hz.

In at least some embodiments, the lower frequency of operation is compensated for by the large magnetic fields near the surface of the magnet 1202 which generates the power. The magnetic fields are sufficiently large to generate adequate power in the generator windings, but fall off very rapidly with distance away from the magnet, such that only very small volumes of tissue are exposed to significant magnetic fields. It may also be the case that these tissues may not be excitable. By contrast, externally generated RF fields may expose relatively larger portions of the body to the field.

In at least some embodiments, the generator windings 902 or 1206-1208 include several layers of very fine, insulated wire. The use of many turns of fine wire allows a relatively high voltage to be generated, and particularly a voltage that is high enough to exceed the voltage drop of the diode rectifier 1104 (i.e., greater than a few tenths of a volt). By contrast, this approach may not work at RF frequencies, where turns may be added to the RF receiver only until the winding self-capacitance drives the self-resonance frequency below the operating frequency.

Figure 14:
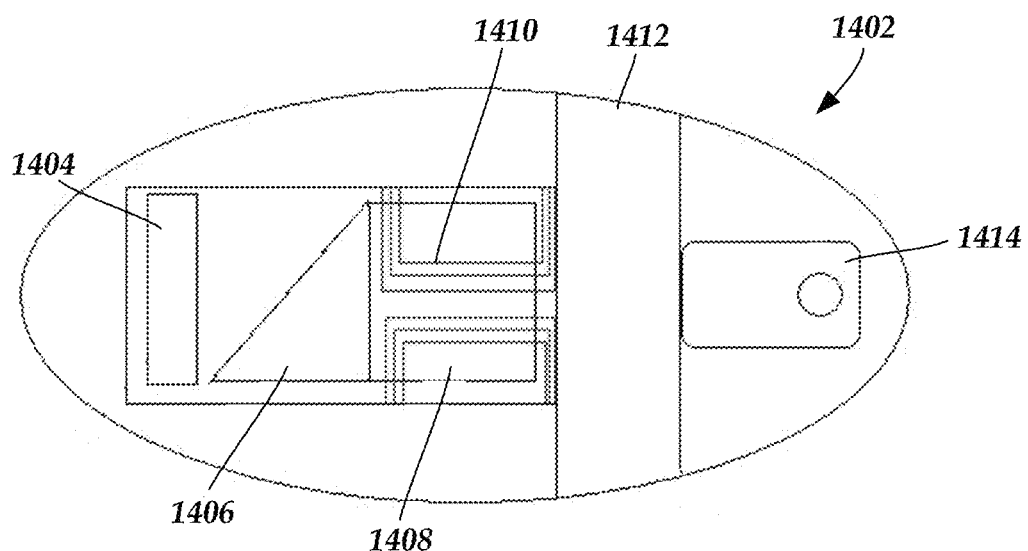
FIG. 14 is a schematic side view of one embodiment of an exemplary imaging pill 1302 suitable for imaging within a patient, according to the invention.

FIG. 14 is a schematic side view of one embodiment of an exemplary imaging pill 1402 suitable for imaging (e.g., IVUS, OCT, or the like) within a patient. The imaging pill 1402 includes an imaging transducer 1404 for transmitting and receiving signals, and a rotating mirror 1406 for reflecting signals propagating to and from the imaging transducer 1404. The imaging pill 1402 also includes a rotatable magnet 1408 and at least one magnetic field winding 1410 that generates a magnetic field at the location of the magnet 1408. In at least some embodiments, the rotation of the magnet 1408 can be used to rotate the mirror 1406. In at least some embodiments, the rotation of the magnet 1408 can be used to enable a localization system to determine the location and orientation of the imaging pill 1402. In at least some embodiments, the rotation of the magnet 1408 can be used generate power for storing in an electronics subsystem 1412. The stored energy can be used for one or more application electronics, such as IVUS (or OCT) imaging, operation of a video camera 1414, or the like.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. A medical device system comprising:
   an imaging pill configured and arranged for ingestion by a patient;
   a housing disposed within the pill;
   a rotatable magnet disposed in the housing and configured to rotate freely relative to the housing;
   at least one magnetic field winding, the magnetic field winding configured and arranged to generate a magnetic field at the location of the magnet, the magnetic field causing rotation of the magnet at a target frequency;
   an array of magnetic field sensors disposed external to the patient, the magnetic field sensors configured and arranged to sense the location and orientation of the magnet in relation to the array of magnetic field sensors;
   electronics for capturing at least one image;
   a power generation system, the power generation system comprising a plurality of layers of wire disposed over the housing;
   an electronic circuit configured and arranged for storing power generated in the layers of wire;
   one or more input leads coupling the plurality of layers of wire to the electronic circuit; and
   one or more output leads coupling the electronic circuit to the electronics for capturing at least one image.

2. The medical device system of claim 1, wherein the electronic circuit further comprises a rectifier for converting AC power to DC power.

3. The medical device system of claim 1, wherein the electronic circuit further comprises a filter.

4. The medical device system of claim 1, wherein the magnet is spherical.

5. The medical device system of claim 1, wherein the housing is spherical.

* * * * *